(12) United States Patent
Jensen et al.

(10) Patent No.: US 6,878,385 B2
(45) Date of Patent: *Apr. 12, 2005

(54) WRINKLE-RESISTANT DRESSING AND GENTLY ADHESIVE COMPOSITION THEREOF

(75) Inventors: Jarl B. Jensen, Nyack, NY (US); Carsten Fredsbo, Rivervale, NJ (US)

(73) Assignee: Jentec, Inc., Northvale, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/229,252

(22) Filed: Jan. 12, 1999

(65) Prior Publication Data

US 2002/0018801 A1 Feb. 14, 2002

(51) Int. Cl.[7] .......................... A61F 13/00; A61K 9/70; A61L 15/00
(52) U.S. Cl. ...................... 424/443; 424/445; 424/446; 424/447; 424/448; 424/449
(58) Field of Search ................................ 424/443, 448, 424/449

(56) References Cited

U.S. PATENT DOCUMENTS

| | | | |
|---|---|---|---|
| 3,339,546 A | * | 9/1967 | Chen |
| 3,896,789 A | * | 7/1975 | Trancik ...................... 128/2 R |
| 4,725,272 A | | 2/1988 | Gale |
| 4,762,124 A | | 8/1988 | Kerch et al. |
| 4,830,856 A | | 5/1989 | Peppers |
| 4,855,335 A | * | 8/1989 | Neperud ...................... 523/111 |
| 4,867,748 A | * | 9/1989 | Samuelsen .................. 604/336 |
| 4,952,618 A | | 8/1990 | Olsen |
| 5,133,821 A | * | 7/1992 | Jensen ......................... 156/245 |
| 5,591,447 A | * | 1/1997 | Jensen ......................... 424/443 |
| 6,010,972 A | * | 1/2000 | Zacharias et al. ........... 442/398 |

OTHER PUBLICATIONS

3M Healthcare., "Tegasorb Ulcer Dressing" Jan. (1989).

* cited by examiner

Primary Examiner—Thurman K. Page
Assistant Examiner—Isis Ghali
(74) Attorney, Agent, or Firm—McDonnell Boehnen Hulbert & Berghoff

(57) ABSTRACT

A dressing for preventing and treating blisters and for treating corns, calluses, warts, and other skin conditions. The dressing has a dressing layer covered by protective cover layer and a release sheet. The dressing has an adhesive composition on a skin-contacting surface. The dressing layer has a thick center portion surrounded by a flange portion. The thick portion has a thickness of less than 1.0 mm. and preferably a thickness of 0.5 mm. The flange portion has a thickness of 0.15 to 0.20 mm. and extends no more than 5.0 mm. from the edge of the thick portion. The configuration of the dressing layer, particularly when used with a hydrocolloid adhesive provides a dressing having wrinkle resistant edges allowing the dressing to be used in areas of the body having high mobility.

20 Claims, 1 Drawing Sheet

WRINKLE-RESISTANT DRESSING AND GENTLY ADHESIVE COMPOSITION THEREOF

FIELD OF THE INVENTION

The present invention relates to the field of dressings that are applied to the human skin, and more particularly, to the field of dressings that function as protective and preventative barriers on the user's skin that may be used while the user is engaged in physical activity. Dressings are commonly used as protective barriers to protect a wound from infection and trauma. Dressings may also be used as preventative barriers that inhibit the formation of blisters, corns, calluses and other skin conditions.

DESCRIPTION OF RELATED ART

The human skin may be subject to certain types of injuries or conditions that may not limit the user's mobility. A sports enthusiast that enjoys sports such as basketball or tennis may be able to play with a blister or a corn. In addition, minor surgical incisions, or minor cuts may not be sufficient to limit normal physical activity. Presently, the methods that exist for treating blisters, corns or small cuts includes the use of a traditional band-aid or regular gauze secured with a tape. Such dressings may be bulky and result in limiting the mobility of the user or preventing the user to carry on a physical activity. The wear-time may also be rather short as the dressing may tend to peel off the skin as the wearer moves and the dressing rubs against the wearer's clothing.

Such traditional methods also suffer from the inability to conform to the shape or contour of the various areas of the human body on which they may be used. The lack of conformability may lead to either lift-off of the dressing from the skin or from detachment at the adhesive. The traditional bandage, for example, lacks the conformability to properly adhere to a small cut on the palm of the hand without lift-off when the user cups the hand.

A further drawback of the use of traditional bandages is the use of pressure sensitive adhesives to attach the bandages to the skin. Such adhesives may irritate the skin causing pain and discomfort. The pain and discomfort may be further aggravated by the removal of hair trapped between the skin and the bandage when the bandage is removed.

Dressings having hydrocolloid adhesives and other moisture-absorbing materials may be used advantageously to treat blisters, corns, calluses, cuts, warts and other such wounds. Jensen, U.S. Pat. No. 5,591,447 (issued Jan. 7, 1997) describes a dressing having an adhesive layer containing one or more hydrocolloids formed with a stair-like contour merging with a peripheral flange of reduced thickness. The peripheral flange and stair-like contour prevents fluid channeling and leakage in the presence of exudate or other moisture that may form at a wound-site. Similar advantages are discussed in Samuelsen, U.S. Pat. No. 4,867,748 (issued Sep. 19, 1989), which describes a dressing containing hydrocolloid-based adhesives and having a bevelled edge.

The dressings in Jensen and in Samuelsen may provide adequate containment of fluid and may extend wear-time in applications involving wounds having heavy exudate, or in situations in which the patient is bed-ridden, or is otherwise limited in mobility. Other types of wound dressings using a similar configuration but different materials such as non-woven, silicone, acrylic, rubber or resin, offer similar advantages.

It has been found however, that when such dressings are used to treat or prevent blisters, corns, calluses, warts and small cuts, wear time, convenience and mobility to the user may be limited. The dressings in Jensen and Samuelsen are subject to wrinkling at the edges that eventually result in roll-up of the dressing. The wrinkling reduces wear time and may annoy users, particularly when the wrinkling at the edges is aggravated by contact with clothing. In addition, the dressings in Jensen and Samuelsen may not conform to the wound-site sufficiently to prevent lift-off.

The dressings in Jensen and Samuelsen also provide no relief to the user during removal. The adhesives used must be strong enough to avoid detachment, and consequently cause pain and remove hair during the removal of the dressing.

It would be desirable to have a dressing that may be used on the human skin for treating or preventing the formation of blisters, corns, warts, calluses, small cuts, etc. without wrinkling at the edges to maximize wear time and comfort.

It would be further desirable to have a dressing that is sufficiently conformable to the contour of the skin site on which it is worn such that the possibility of detachment is minimized.

It would be further desirable to have a dressing that adheres to the skin without causing pain and removal of hair during removal of the dressing.

BRIEF DESCRIPTION OF THE DRAWINGS

Presently preferred embodiments of the invention are described below in conjunction with the appended drawing figures, wherein like reference numerals refer to like elements in the various figures, and wherein.

DETAILED DESCRIPTION OF THE PREFERRED EMBODIMENT

Figure 1:
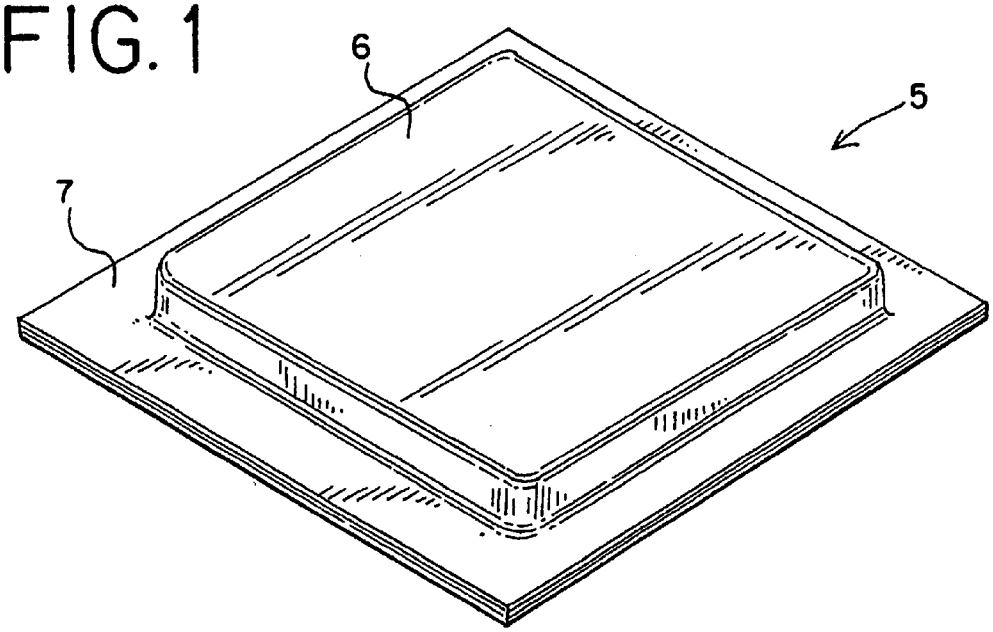
FIG. 1 represents a perspective view of a dressing according to a preferred embodiment of the present invention.

FIG. 1 shows an individual dressing 5 according to a preferred embodiment of the present invention. This dressing 5 has a thick portion 6 and a thin flange portion 7.

The dressing 5 may be a wound dressing that may be used to treat or prevent the formation of blisters, corns, calluses, small cuts, warts, or other such conditions on the human skin. The shape of the dressing 5 in FIG. 1 is rectangular, however, the dressing 5 may have any shape, and may also include an inner hole for use as an ostomy wafer.

Figure 2:
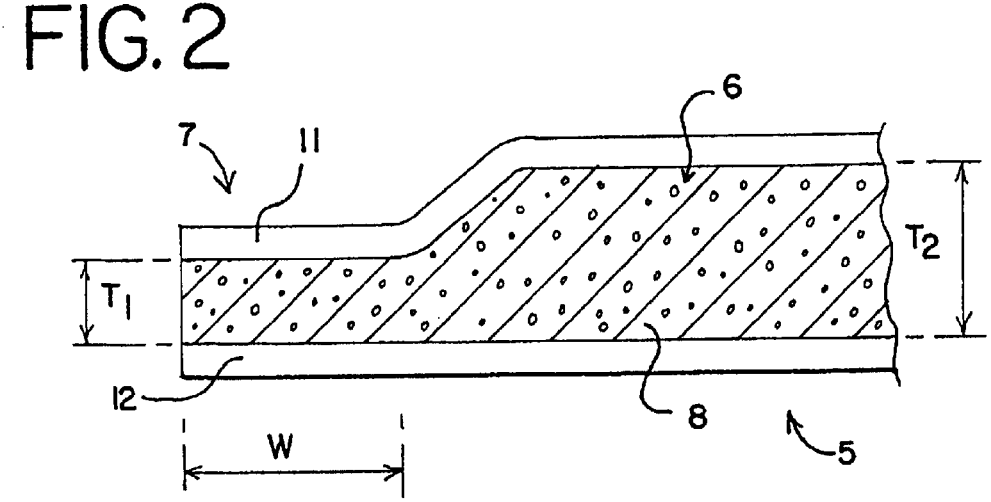
FIG. 2 represents a fragmentary cross-sectional view of the device in FIG. 1.

FIG. 2 shows a fragmentary cross-sectional view of one example of the dressing 5 shown in FIG. 1. The dressing 5 in FIG. 2 includes a dressing layer 8, a release sheet 12, and a protective cover layer 11. The dressing layer 8 preferably makes contact with an area of skin at a skin-contacting surface 9 and protects the skin from abrasion and exposure to infectious particles. The dressing layer 8 may include a hydrocolloid-adhesive, a hydrogel, a silicone material, a natural or synthetic rubber, or any other suitable dressing material. The material chosen for the dressing layer 8 may be adhesive, or a pressure sensitive adhesive may be added to the skin-contacting surface 9 to secure the dressing layer 8 to the skin. In a one embodiment in which moisture absorption is a desired feature, the dressing layer 8 comprises a hydrocolloid-adhesive material of about 30% to 60% by weight of a water-soluble hydrocolloid, or a mixture of such hydrocolloids. The hydrocolloid may include calcium carboxymethylcellulose, pectin, gelatin, high molecular weight carbowax, carboxypolymethylene, and polyvinyl alcohol. The hydrocolloid may be mixed with about 10% to 30% by weight of a water-insoluble, viscous elastomer. The elastomer may include polyisobutylene, natural rubber, silicone rubber, arcylonitrile rubber, and polyurethane rubber.

In a preferred embodiment that uses a hydrocolloid adhesive, the dressing layer 8 comprises from 25 to 50% by weight of hydrocolloid, from 10 to 30% of elastomer (styrene, Kraton, olefin-styrene), from 20 to 50% of hydrocarbon resin, and from 0 to 30% of oily extender. The elastomer may include styrene-olefin-styrene.

Alternatively, however, no hydrocolloid is included in the composition of the dressing layer 8. The absorptive properties of hydrocolloids may be desirable in some applications. However, embodiments of the present invention advantageously provide maximum effective wear-time without limiting the user's mobility. In general, any soft material that is soft, conformable, elastic, tacky and has a low modulus may be used.

Examples of alternative compositions may be found in "Wound Dressings", Jensen, Jarl et al., filed on Jan. 11, 1999, which is incorporated herein by reference in its entirety. For example, in one embodiment, the dressing layer 8 comprises 30% by weight elastomer, 30% by weight non-polar oily extender (i.e. mineral oil) and 40% hydrocarbon tackifier resin (i.e. Foral-85). The dressing layer 8 comprising this composition advantageously conforms to the skin dressing site without sticking to hair or damaging skin. Such advantages may be realized using as much as 60% by weight of oily extender. These advantages combined with the conformability available to the dressing layer 8 having the physical dimensions described below provide a dressing that prevents or treats blisters, calluses, corns or warts without limiting physical activity or irritating the skin.

Another alternative composition may include DL-α-tocopheryl acetate as an adhesive agent. For example, a composition comprising 50% elastomer (preferably Kraton™), 20% hydrocarbon tackifier resin (preferably, Foral 85™), and 30% DL-α-tocopheryl acetate may provide a dressing 5 that is soft, gently adhesive and will not stick to hair or damage skin upon removal. DL-α-tocopheryl acetate may also be used in a composition having a hydrocolloid for absorptive properties. For example, a composition having 30% elastomer, 10% hydrocarbon tackifier resin, 40% hydrocolloid (e.g. carbomethylcellulose) and 20% DL-α-tocopheryl acetate provides a dressing having gently adhesive and absorptive properties.

The flange portion 7 of the dressing layer 8, in embodiments of the present invention, has a thickness, $T_1$, that is greater than ¼ the thickness of thick portion 6. In a preferred embodiment, the thick portion 6 has a thickness $T_2$ is 0.5 mm. and no thicker than 1.0 mm.; and the flange portion 7 is 0.15 mm.–0.20 mm. and no thicker than 0.3 mm. In addition, in a preferred embodiment, the flange portion is ⅓ the thickness of the thick portion 6. The thickness optimally provides a degree of stability, yet remains flexible, soft and conformable.

Figure 3:
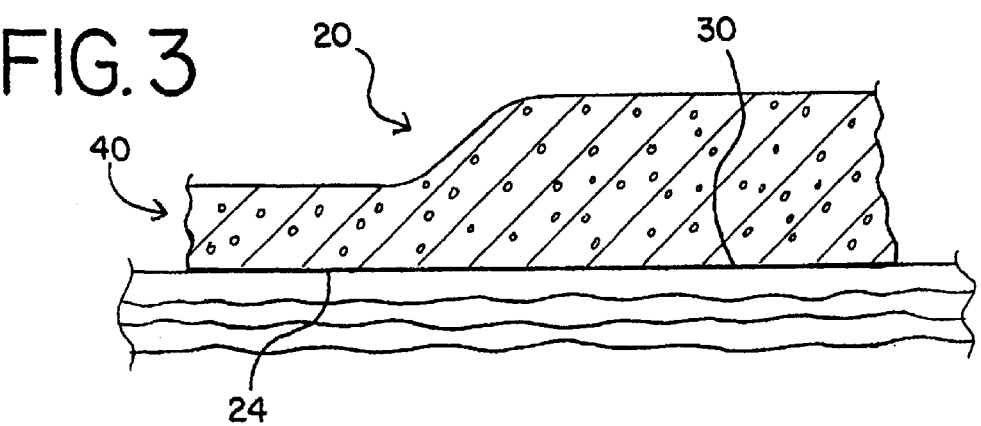
FIG. 3 shows a dressing with a wrinkled edge.

The configurations described with reference to FIG. 2 have been compared with other known configurations in a test that illustrates the effectiveness of the various configurations in protecting the skin under vigorous physical activity. In one test, each of the various configurations were made with the same materials and placed on the palm of the hand. The hand was then subjected to vigorous movement to determine how long it takes for wrinkles and lift off to occur. One product configuration tested is shown in FIG. 3. FIG. 3 shows a fragmentary cross-sectional view of a large flange dressing 20 applied to a skin surface 30. The large flange dressing 20 includes a large flange 24 of approximately 5 mm and has a thickness at its center of approximately 0.5 mm. Within approximately one minute of application, the edge of the flange portion 24 begins to lift off such that it tends to roll off as shown at 40. Within approximately five minutes, the dressing 20 begins to wrinkle or lift off in streaks of lines across the area of the dressing 20. The lift off and wrinkling may be aggravated during wear by frictional contact with clothing.

The results observed using thicker products having a border region as disclosed in Samuelsen were not as good. Such products have a thickness at the center portion that is greater than 1 mm. and have a greater than 4 to 1 relationship between the thickness of the center region and the thickness of the border region. When placed on the palm of the hands and subjected to vigorous hand movement, the thicker products were falling off within approximately five minutes.

Using thinner products without a border was also found to be unacceptable. Such products wrinkled and lifted off within one minute of application. The advantage of the dressing 8 in FIG. 2 is that the flange portion 7, which extends a distance W that is less than 5.0 mm., helps prevent the lift off and wrinkling shown at 40 in FIG. 3. A configuration of the dressing 5 subjected to the test above was able to last up to approximately five minutes with no wrinkling or lift off at all. Minor lift off was observed after five minutes, however, overall usability under vigorous physical activity was observed to be greater than with the other configurations.

The dressing may be packaged in a variety of ways that are suitable to the intended application. In a preferred embodiment, a protective covering and a release sheet are attached to the dressing. Referring back to FIG. 2, the release sheet 12 is a release sheet that is to be removed during the application of the dressing. In a wound dressing, the release sheet 12 is preferably made of a silicone release paper or other flexible material treated for easy removal from the dressing layer 8. Other materials include polyester and polypropylene films.

The protective cover layer 11 may be provided as a protective covering for the dressing layer 8 on the side opposite the skin-contacting surface 9. In a wound dressing, the protective cover layer 11 may be made of co-polyester, ethyl vinyl acetate, polyether block amide, polyethylene pulp non-woven, polyurethane film, polyethylene film, non-woven, or other suitable film may be used as a protective cover for the dressing layer 8. Other materials may be used for the protective cover layer 11 depending on the function of the dressing layer 8.

The dressing 5 described herein may be manufactured using traditional methods of dressing manufacture. For example, Jensen, U.S. Pat. No. 5,133,821, Samuelsen U.S. Pat. No. 4,867,748 and Jensen, et al. U.S. patent application Ser. No. 09/184,811 (incorporated by reference herein) describe methods that may be used to manufacture the dressing 5.

Persons of ordinary skill in the art will appreciate that variations may be made without departure from the scope and spirit of the invention. This true scope and spirit is defined by the appended claims, interpreted in light of the foregoing.

We claim:

1. An improved dressing comprising a dressing layer having a skin-contacting surface, the dressing layer having a hydrocolloid adhesive comprising a hydrocolloid and an elastomer, the improvement comprising:
   the dressing layer having a central, thick portion and a peripheral flange portion of a thickness less than the thick portion, the peripheral flange portion extending a distance of less than 3.5 mm. and the flange portion having a thickness of at least ⅓ the thickness of the thick portion, the thick portion being no more than 1.0 mm. thick.

2. An improved dressing as claimed in claim 1 wherein the dressing layer comprises a material selected from the group consisting of a hydrocolloid adhesive, silicone, hydrogel, acrylic, natural rubber, synthetic rubber and resin.

3. An Improved dressing as claimed in claim 1 wherein the dressing layer comprises a hydrocolloid adhesive comprising approximately 30% to approximately 60% by weight of hydrocolloid or a mixture of hydrocolloids selected from the group consisting of calcium carboxymethylcellulose, pectin, gelatin, high molecular weight carbowax, carboxypolymethylene, and polyvinyl alcohol, end approximately 10% to approximately 30% by weight of elastomer selected from the group consisting of polyisobutylene, natural rubber, silicone rubber, acrylonitrile rubber, and polyurethane rubber.

4. An improved dressing as claimed in claim 1 wherein the dressing layer comprises:
   approximately 25% to approximately 50% by weight of hydrocolloid;
   approximately 10% to approximately 30% by weight of elastomer; and
   approximately 20% to approximately 50% of hydrocarbon tackifier resin.

5. An improved dressing as claimed in claim 4 comprising up to 30% of oily extender.

6. An improved dressing as claimed in claim 5 wherein the oily extender is mineral oil.

7. An improved dressing as claimed in claim 4 wherein the elastomer is a made of styrene-olefin-styrene.

8. An improved dressing as claimed in claim 1 wherein the dressing layer comprises:
   approximately 10% to approximately 35% by weight elastomer;
   approximately 2% to approximately 60% by weight non-polar oily extender and
   approximately 20% to approximately 80% hydrocarbon tackifier resin.

9. An improved dressing as claimed in claim 8 wherein the dressing layer comprises:
   approximately 30% by weight of elastomer;
   approximately 30% by weight of non-polar oily extender; and
   approximately 40% by weight of hydrocarbon tackifier resin.

10. An improved dressing as claimed in claim 8 wherein the non-polar oily extender comprises a mineral oil.

11. An Improved dressing as claimed in claim 1 wherein the dressing layer comprises DL-α-tocopheryl acetate as an adhesive agent.

12. An improved dressing as claimed in claim 1 wherein the dressing layer comprises:
   approximately 50% elastomer;
   approximately 20% hydrocarbon tackifier resin; and
   approximately 30% DL-α-tocopheryl acetate.

13. An improved dressing as claimed in claim 12 wherein the elastomer is styrene-olefin-styrene.

14. An improved dressing as claimed in claim 1 wherein the dressing layer comprises:
   approximately 30% elastomer;
   approximately 10% hydrocarbon tackifier resin;
   approximately 40% hydrocolloid; and
   approximately 20% DL-α-tocopheryl acetate.

15. An improved dressing as claimed in claim 14 wherein the elastomer is styrene-olefin-styrene.

16. An improve dressing as claimed in claim 1 wherein the thick portion is 0.5 and the flange portion is at least ⅓ of the thickness of the thick portion and no more than 0.20 mm thick.

17. An improved dressing as claimed in claim 16 wherein the flange portion extends a distance of 3.0 mm. from the edge of the thick portion.

18. An improved dressing as claimed in claim 1 wherein the dressing further comprises:
   a release sheet; and
   a protective cover layer, the release sheet being attached to the skin-contacting surface of the dressing layer and the protective cover layer being attached to the side opposite the skin-contacting surface of the dressing layer.

19. An improved dressing as claimed in claim 18 wherein the protective cover layer comprises a material selected from the group consisting of: co-polyester, ethyl vinyl acetate, polyether block amide, polyethylene pulp non woven, polyurethane film, polyethylene film, and non-woven.

20. An improved dressing as claimed in claim 18 wherein the release sheet comprises a material selected from the group consisting of: polyester film, polyproylene film, and silicone release paper.

* * * * *